United States Patent [19]

Swanson

[11] 4,027,535
[45] June 7, 1977

[54] MANUAL THRUST GAUGE

[76] Inventor: Erik Swanson, 15939 NW. 40 Court, Opa Locka, Fla. 33054

[22] Filed: Feb. 2, 1976

[21] Appl. No.: 654,713

[52] U.S. Cl. .................................. 73/381; 73/491; 73/514
[51] Int. Cl.² ...................... G01L 5/06; G01P 15/02
[58] Field of Search ............................ 73/379–381, 73/514, 491–492

[56] References Cited

UNITED STATES PATENTS

| 2,903,320 | 9/1959 | De Changy | 73/514 X |
| 2,924,442 | 2/1960 | Gray | 73/514 X |
| 3,815,427 | 6/1974 | Gladstone | 73/514 X |

FOREIGN PATENTS OR APPLICATIONS

| 1,064,801 | 5/1954 | France | 73/514 |
| 271,020 | 5/1927 | United Kingdom | 73/514 |

Primary Examiner—Richard C. Queisser
Assistant Examiner—Charles Gorenstein
Attorney, Agent, or Firm—Ralph S. Branscomb

[57] ABSTRACT

A manual thrust gauge is comprised of a frame having either a hand grip or a wrist strap, there being a weighted member movably mounted to the frame and restrained by a spring which moves relative to a fixed member, one of these members comprising a scale and the other being a pointer and the movable member being releasably detained in any one of several displaced positions so that the user may thrust his hand as in a boxing punch, a karate chop or the like and the pointer will register on the scale the relative acceleration or deceleration of the punch.

8 Claims, 13 Drawing Figures

MANUAL THRUST GAUGE

BACKGROUND OF THE INVENTION

The invention relates to sports, games, and measuring devices.

It is difficult for the participants in practice for combat sports, in which the hands and arms are used as weapons, to determine the force with which a blow is struck. Presently this force is roughly judged by the reaction of a punching bag to a blow or an equivalent reaction pertaining to another sport, but this judgment is clearly rough and does not give the participant an accurate idea of whether his stroke is improving or worsening, and can be somewhat painful to the participant in karate practice who overestimates the number of bricks he can chop through.

SUMMARY OF THE INVENTION

The invention in its several embodiments provides a manual thrust gauge both for use in serious sporting practice and for the entertainment of children. The gauge may be strapped to the participant's wrist to free the knuckles during boxing practice, or utilized with a hand grip for karate and the like, the mechanism employed being essentially an accelerometer. In one embodiment a ratchet-detained eccentrically weighted disc having a graduated dial connected thereto and registering with a fixed pointer is used, and other embodiments include a weighted resilient spring arm having a pointer integral with the free end thereof to register with a fixed scale. In some instances it would be desirable that the entire accelerometer mechanism be angularly adjustable relative to the hand or wrist attachment so that strokes in different directions could be accurately measured.

DETAILED DESCRIPTION OF THE PREFERRED EMBODIMENTS

Figure 1:
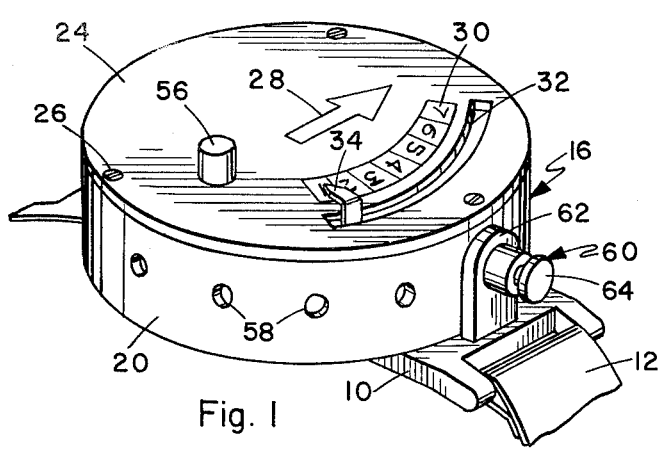
FIG. 1 is a perspective view of one form of the thrust gauge.

The invention as illustrated in FIGS. 1 through 5 includes a frame member 10 to which is attached a wrist band 12 for connecting the device to the wrist of the arm 14 of the user. A casing 16 is attached to the frame either rigidly or, as shown, rotatably, by means of a screw 18 or the equivalent for a purpose made clear below. This casing has a circular sidewall 20, a bottom wall 22, and a cover plate 24 secured to bosses in the sidewall by screws 26, or the like. As can be seen in FIG. 1, the cover plate 24 displays an arrow 28 which indicates the direction of thrust in which the deceleration will be most accurately measured, and a graduated scale 30 is also displayed along an arcuate slot 32 through which an indicator member or pointer 34 projects to register with the scale.

Figure 2:
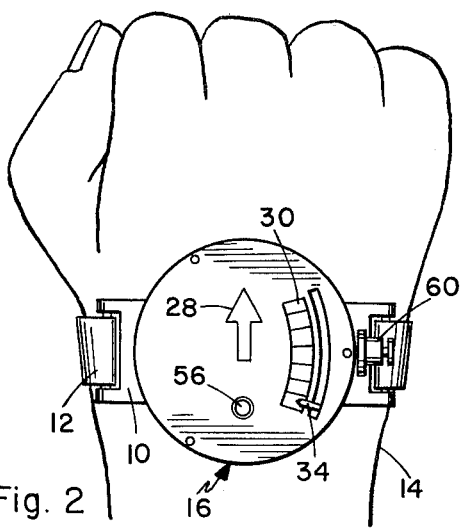
FIG. 2 illustrates the device as worn on a wrist.
Figure 3:
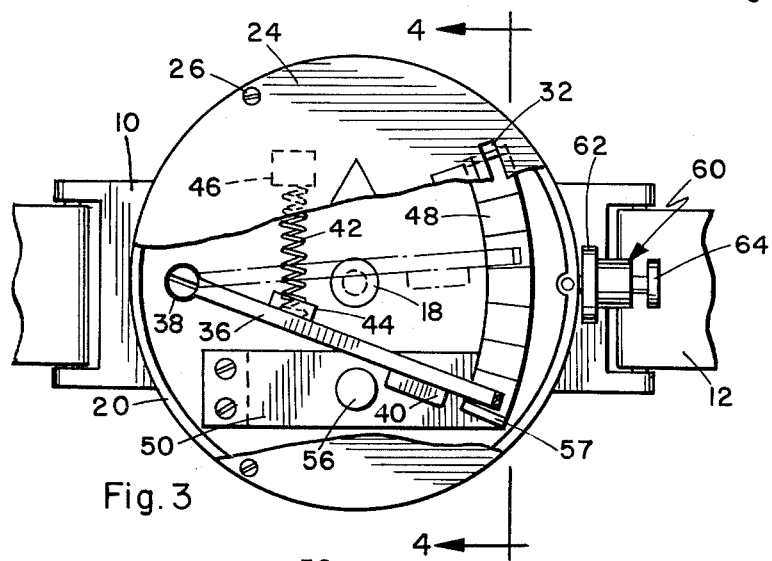
FIG. 3 is a top plan view of the gauge with portions cut away.
Figure 4:
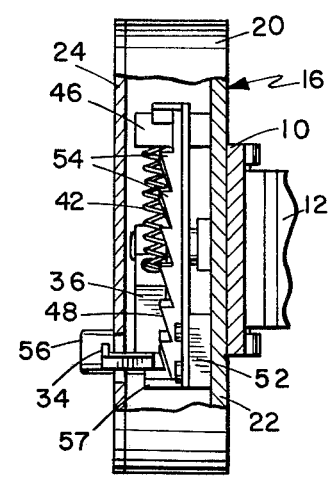
FIG. 4 is a sectional view taken on line 4—4 of FIG. 3.
Figure 5:
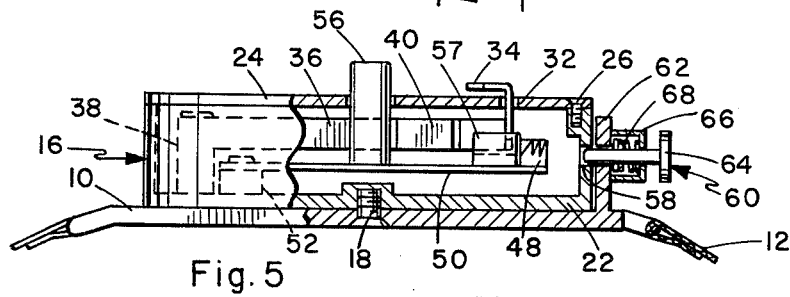
FIG. 5 is a side elevation view, partially cut away, of the structure of FIG. 3.

The interior mechanism of the casing, illustrated in FIGS. 3–5, includes a swing arm 36 which is pivoted at one end to a post 38 connected to the bottom wall of the casing and the free swinging end of this swing arm carries the indicator 34. A weight 40 is provided near the pointer end of the swing arm, and a bias means, illustrated as a compression coil spring 42 captured between a cup 44 mounted on the swing arm and a post 46 extended from the bottom wall of the casing, is included to resist the forward motion of the swing as the latter is urged against the spring force by the weight 40 in response to an arm thrust of the user. Thus because of the obvious relation between the pointer 34 and the scale 30, the harder the striking force of the fist as illustrated in FIG. 2 against a punching bag or the like or into the air, the greater will be the deceleration of the fist and thus the farther will be the travel of the pointer along the scale.

Since clearly the return of the pointer 34 subsequent to a punch would be too quick to enable a sportsman to obtain an accurate scale reading, a releasable detent is included to arrest the motion of the swing arm at its forwardmost position and prevent the return thereof. This releasable detent comprises a ratchet blade 48 illustrated as arcuate in shape which is supported at one end by a preferably integral resilient member 50 mounted to the casing at 52, this resilient member biasing the ratchet blade upwardly so that the teeth 54 thereof successively engage the mobile end of the swing arm as same moves forwardly and retains the swing arm in its forwardmost position until the ratchet blade is depressed by means of a release button 56 extending from the resilient support member 50 up through an opening in the cover plate of the casing. The ratchet blade is aslo provided with an upstruck stop 57 to prevent the reverse movement of the pointer below the zero position during a thrust. It should be clear from the above description that a sportsman or a child in play may strap a thrust gauge to his wrist, execute a punch or chop, observe the strength of the punch or chop by noting the point of registry of the pointer on the scale, and then reset the thrust gauge for the next action by depressing the button 56.

Although the orientation of the thrust gauge relative to the wrist and fist shown in FIG. 2 would probably be appropriate for a boxing punch, if a sidewise karate-type punch were executed, clearly the thrust gauge would register little, if any. To account for this the gauge casing is made rotatably adjustable on the frame 10 as already mentioned. To prevent the casing from free-wheeling, it could be frictionally fitted against the frame or otherwise infinitely adjustable, but in the form shown, the sidewall 20 of the casing is provided with a plurality of evenly spaced holes 58 which cooperate with a spring-loaded detent 60 supported on a bracket 62 mounted to the thrust gauge frame, this detent including a pull pin 64 extending through a housing 66 for a spring 68 to releasably and selectively engage the holes 58 in obvious fashion to permit the discrete angular adjustment of the casing on the frame and thus relative to the arm.

Figure 6:
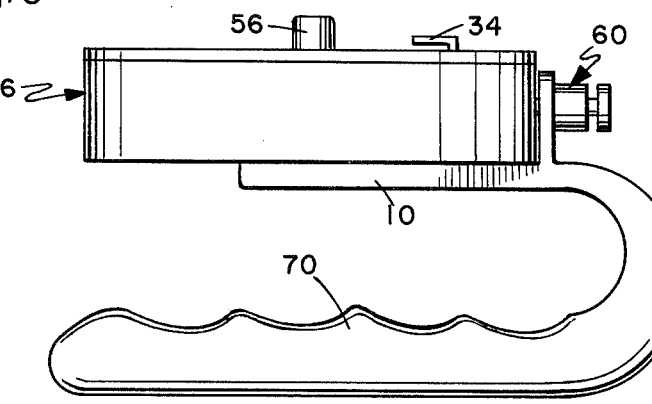
FIG. 6 illustrates the gauge mounted on a hand grip.

In a slight modification of the embodiment of the thrust gauge described above, a hand grip 70 may be attached to the frame 10 replacing the strap or wrist band 12, as illustrated in FIG. 6. The orientation of the thrust gauge casing could be modified from that shown in FIG. 6 such that the casing and the curved hand grip lie in the same general plane.

Figure 7:
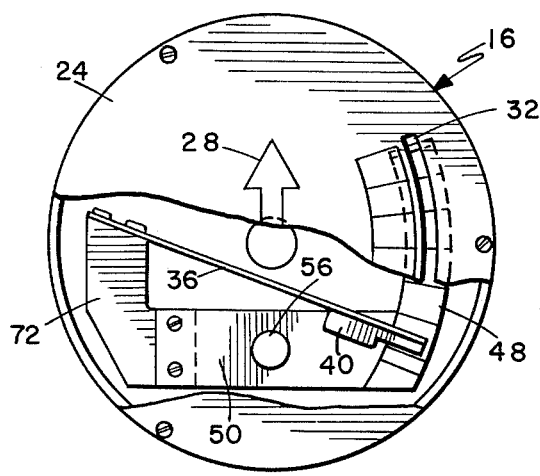
FIG. 7 is a top plan view, partially cut away, of an alternative mechanism.

In another slight modification of the working mechanism of the device illustrated in FIG. 7, the swing arm 36 is itself made resilient to replace the spring 42 in the prior arrangement. The mounted end of ths swing arm is connected to an upstruck portion of an extension 74 of the resilient member 50. This arrangement would probably have an economic advantage in manufacture.

Figure 8:
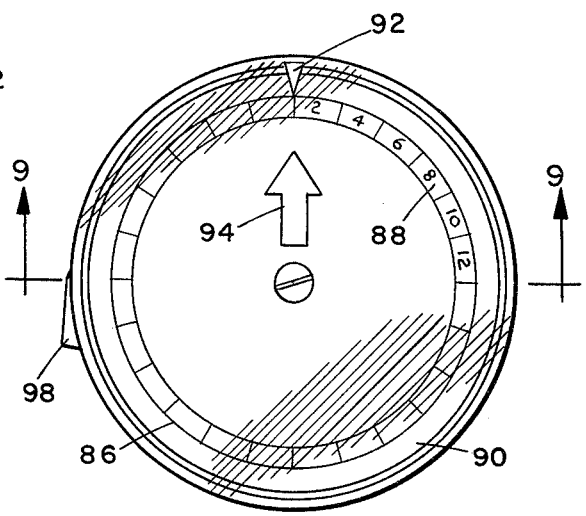
FIG. 8 is a top plan view of a further form of the thrust gauge.
Figure 9:
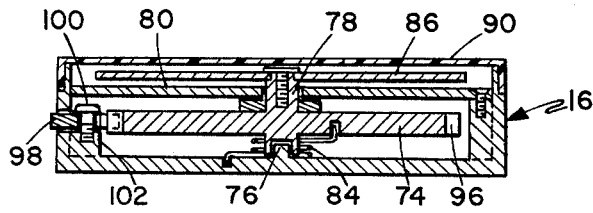
FIG. 9 is a sectional view taken on line 9—9 of FIG. 8.
Figure 10:
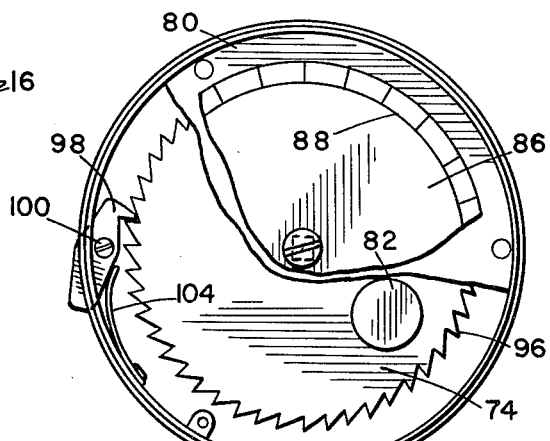
FIG. 10 is a top plan view, partially cut away and with the cover removed, of the structure of FIG. 9.

In yet another embodiment of the invention illustrated in FIGS. 8-10, a disc 74 is rotatably mounted within the casing by means of a central stub axle 76 extending from the bottom wall and over which a partially hollowed disc shaft 78 seats, and a retaining plate 80 which is secured to the casing walls. The disc is eccentrically weighted at 82 and a helical spring 84 encircling the disc axle applies an angular bias between the casing's bottom and the disc to resist the inertia of the weight in use. The central shaft of the disc extends through a central opening in the retaining plate and to the upper end of the shaft is mounted a dial 86 as best seen in plan view in FIG. 8. The dial is provided with a scale 88 which is shown as continuous for reasons of appearance but clearly need not extend over more than a portion of the circular arc. Covering this dial and completing the enclosure of the casing is a cover plate or cap 90 secured to the sidewall of the casing. This cover cap is transparent, at least in its planar portions, and includes an indicator arrow 92 to register with the scale 88, and may further include a directional arrow 94 to indicate proper thrust direction.

It can be seen that whereas in the prior embodiment of the invention the pointer or indicator mounted on the swing arm moved relative to a fixed scale, in the embodiment disclosed in FIGS. 8-10 the scale moves relative to the pointer. In order to arrest the motion of the disc at its furtherest point of registry, the circumference of the disc is toothed as at 96 and a pawl 98 is pivoted on a screw or rivet 100 to a post 102 extending from the casing bottom. A leaf spring or the like 104 biases the pawl into engagement with the toothed perimeter of the disc, and the extended end of the pawl projects externally of the casing wall so that it may be depressed to release the disc. The pawl prevents reverse rotation of the disc and locks the disc at the instant of maximum deceleration.

It will be noted that although in the embodiment described immediately above, the scale bearing dial 86 is removed from the weighted disc 82, it would in fact be possible to print the scale directly on the disc with a slight modification of the support structure in the casing.

Figure 11:
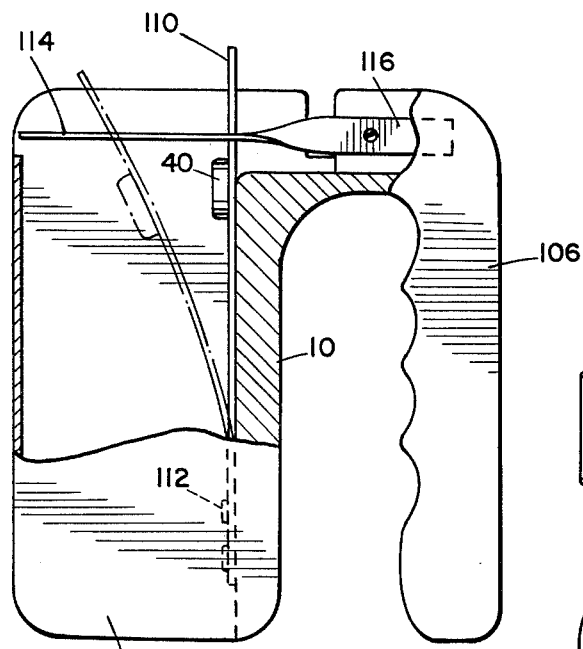
FIG. 11 is a side elevation view, partially cut away, of a hand grip configuration of the gauge.
Figure 12:
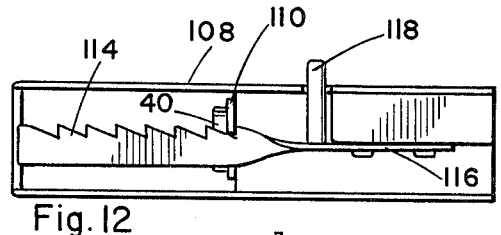
FIG. 12 is a top plan view of the structure of FIG. 11.
Figure 13:
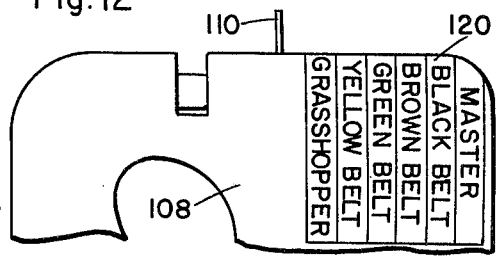
FIG. 13 is an elevation view taken along lines 13—13 of FIG. 12.

In the modification illustrated in FIGS. 11 through 13, the frame 10 of the thrust gauge has a hand grip 106 extended therefrom similar to that illustrated in FIG. 6 and a generally rectangular casing 108 is mounted to the frame. A swing arm 110 is riveted as at 112 to the frame, this swing arm being resilient and having the weight 40 attached to the free end thereof. The end portion of the swing arm is selectively engaged on the teeth of a ratchet blade 114 which has an orthogonally twisted portion 116 to permit the ratchet blade to be easily deflected out of engagement with the swing arm upon depressing the release button 118 which extends through the side of the casing. The end of the swing arm acts as an indicator or pointer and registers with a scale 120 which is printed along the sides of the thrust gauge casing. It will be noted that whereas the scale illustrated in FIG. 8 is numbered and intended to indicate roughly acceleration in miles per hour per hour, the scale on the embodiment in FIGS. 11-13 is graduated by indicating thereon the various colors of belts associated with different degrees of skill in karate. Clearly this last embodiment is the most economical and is conceived more for use as a child's toy than by sportsmen, and the scale imprinted thereon as indicated in FIG. 13, adds to the enjoyment of playing with the thrust gauge.

I claim:

1. A manual thrust gauge comprising:
   a. a frame;
   b. means mounted on said frame for engagement on a human extremity;
   c. two cooperating gauging members comprising a scale member and an indicator member both mounted on said frame, one of said members being weighted and having one portion anchored to said frame and another portion movable relative to the other of said members such that said indicator is registerable at different positions along said scale;
   d. bias means urging said one member in one direction relative to the other of said members;
   e. a releasable detent for detaining said one member against said bias means at a plurality of selectable positions relative to the other of said members, whereby upon engaging said thrust gauge on a human extremity and striking out with same, said one member will be moved relative to said other member and be releasably engaged at a position relative thereto such that the indicator will point out on said scale member the relative striking force.

2. Structure according to claim 1 wherein said means to engage a human extremity comprises a wrist strap.

3. Structure according to claim 1 wherein said means to engage a human extremity comprises an elongated hand grip.

4. Structure according to claim 1 wherein said scale member comprises a face plate mounted on said frame having said scales displayed thereon and including a slot defined in said face plate along said scale, and said indicator member is movably mounted in said frame and extends forwardly through said slot to register with said scale.

5. Structure according to claim 4 wherein said indicator member is movable relative to said scale member and said releasable detent comprises a resilient toothed ratchet blade mounted to said frame and biased against said indicator such that said indicator is detained by the individual teeth of said ratchet blade, and including an extension of said ratchet blade operable to depress same and release said indicator member.

6. Structure according to claim 5 wherein said members, said bias means, and said releasable detent are mounted in a casing which is rotatably mounted on said frame such that by rotatably adjusting said casing, said thrust gauge is effective for different thrust directions.

7. Structure according to claim 1 wherein said indicator member is mounted on one end of a resilient spring arm having a weight mounted thereon, the other end of said spring arm being rigidly mounted to said frame whereby said spring arm comprises said bias means and said indicator member is movable relative to said scale member.

8. Structure according to claim 1 wherein said scale member comprises a disc having an eccentric weight and a toothed perimeter, and a scale-displaying dial mounted coaxially with said disc, said disc being rotatably mounted to said frame and said indicator member being rigidly mounted to said frame in registry with the scale displayed on said dial, and said releasable detent comprises a pawl movably mounted on said frame and biased against said toothed perimeter.

* * * * *